(12) United States Patent
Schiemann et al.

(10) Patent No.: US 8,552,001 B2
(45) Date of Patent: Oct. 8, 2013

(54) SULFOXIDE DERIVATIVES FOR THE TREATMENT OF TUMORS

(75) Inventors: Kai Schiemann, Seeheim-Jugenheim (DE); Melanie Schultz, Darmstadt (DE); Wolfgang Staehle, Ingelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/501,467

(22) PCT Filed: Sep. 14, 2010

(86) PCT No.: PCT/EP2010/005641
§ 371 (c)(1),
(2), (4) Date: Apr. 12, 2012

(87) PCT Pub. No.: WO2011/044978
PCT Pub. Date: Apr. 21, 2011

(65) Prior Publication Data
US 2012/0202827 A1    Aug. 9, 2012

(30) Foreign Application Priority Data

Oct. 13, 2009  (DE) .......................... 10 2009 049 211

(51) Int. Cl.
*A61K 31/496* (2006.01)
*C07D 413/12* (2006.01)
*C07D 403/12* (2006.01)

(52) U.S. Cl.
USPC ................ 514/254.02; 514/254.06; 544/368; 544/366

(58) Field of Classification Search
USPC ................ 544/368, 366; 514/254.02, 254.06
See application file for complete search history.

(56) References Cited

U.S. PATENT DOCUMENTS
2010/0222341 A1    9/2010   Schiemann et al.

FOREIGN PATENT DOCUMENTS
WO    WO 2009/046841 A2    4/2009

OTHER PUBLICATIONS

Vippagunta et al., Crystalline solids, 2001, Advanced Drug Delivery Reviews, 48, pp. 3 and 18.*
Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
International Search Report of PCT/EP2010/005641 (Dec. 15, 2010).

* cited by examiner

*Primary Examiner* — Kristin Vajda
(74) *Attorney, Agent, or Firm* — Millen, White, Zelano & Branigan, P.C.

(57) ABSTRACT

Sulfoxide derivatives of the formula Ia to Im as described, and pharmaceutically usable salts, solvates, enantiomers, tautomers and stereoisomers thereof, including mixtures thereof in all ratios, for the treatment of tumors.

20 Claims, No Drawings

SULFOXIDE DERIVATIVES FOR THE TREATMENT OF TUMORS

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are accompanied by an increase in the lysophosphatidic acid level, furthermore to pharmaceutical compositions which comprise these compounds.

In detail, the present invention relates to compounds which preferably inhibit one or more enzymes which regulate and/or modulate the lysophosphatidic acid (LPA) level, to compositions which comprise these compounds, and to processes for the use thereof for the treatment of diseases and complaints, such as angiogenesis, cancer, tumour formation, growth and propagation, arteriosclerosis, ocular diseases, choroidal neovascularisation and diabetic retinopathy, inflammatory diseases, arthritis, neuro-degeneration, restenosis, wound healing or transplant rejection. In particular, the compounds according to the invention are suitable for the therapy or prophylaxis of cancer diseases.

Autotaxin (ATX) is an enzyme which is responsible for the increase in the lysophosphatidic acid level in ascites and plasma (Xu et al. 1995, Clinical Cancer Research Vol. 1, page 1223 and Xu et al. 1995, Biochem. J. Vol-309, page 933). ATX converts lysophatidylcholine (LPC) into lysophosphatidic acid (Tokumura et al. 2002, J. Biol. Chem., Vol 277, page 39436 and Umezu-Gozo et al. 2002, J. Biol. Chem., Vol. 158, page 227) LPA is an intercellular lipid mediator which influences a multiplicity of biological and biochemical processes, such as, for example, smooth muscle contraction, thrombocyte aggregation and apoptosis (Tigyi et al. 2003 Prog. Lipid Res. Vol 42, page. 498 and Mills et al. 2003 Nat. Rev. Cancer Vol. 3, page 582 and Lynch et al. 2001 Prost. Lipid Med. Vol. 64, page 33). In addition, LPA can be found in increased concentrations in plasma and ascites fluid from ovarian cancer patients in the early and late phase. LPA plays a role there in tumour cell proliferation and invasion thereof into neighbouring tissue, which can result in metastasisation (Xu et al. 1995, Clinical Cancer Research Vol. 1, page 1223 and Xu et al. 1995, Biochem. J. Vol-309, page 933). These processes are switched on by the activation by LPA of G protein-coupled receptors (Contos et al. 2000, Mol. Pharm. Vol 58, page. 1188).

For this reason, it is desirable to lower the LPA level for the treatment of tumour patients. This can be achieved by the inhibition of enzymes which are involved in LPA biosynthesis, such as, for example, autotaxin (ATX, Sano et al. 2002, J. Biol. Chem. Vol. 277, page 21197 and Aoki et al. 2003, J. Biol. Chem. Vol. 277 page 48737). Autotaxin belongs to the enzyme family of the nucleotides pyrophosphatases and phosphodiesterases (Goding et al. 1998, Immunol. Rev. Vol. 161, page 11) and represents an important starting point in antitumour therapy (Mills et al. 2003 Nat. Rev. Cancer Vol. 3, page 582 and Goto et al. 2004 J. Cell. Biochem. Vol. 92, page 1115) since it is expressed to an increased extent in tumours and causes tumour cell proliferation and invasion thereof into neighbouring tissue, which can result in metastasisation (Nam et al. 2000, Oncogene, Vol. 19 page 241). In addition, autotaxin together with other angiogenetic factors causes blood vessel formation in the course of angiogenesis (Nam et al. 2001, Cancer Res. Vol. 61 page. 6938). Angiogenesis is an important process in tumour growth, which ensures supply of the tumour with nutrients. For this reason, inhibition of angiogenesis is an important starting point in cancer and tumour therapy, in which the aim is to starve the tumour (Folkman, 2007, Nature Reviews Drug Discovery Vol. 6, page 273-286). Furthermore, autotaxin controls the migration of T cells into secondary lymphatic organs by means of the conversion of LPC into LPA. Naïve T cells constantly migrate between blood and secondary lymphatic organs, the lymph nodes, in the healthy organism. In order to migrate from the bloodstream into a lymph node, the T cells must overcome specialised blood vessels, so-called high endothelial venules (HEV). Autotaxin is involved in this process. HEV cells secrete autotaxin into the bloodstream. This binds to T cells and converts LPC into LPA on the surface thereof. LPA in turn binds to specific receptors on the surface of the T cells and increases their ability to migrate into lymph nodes. Treatment of T cells with an autotaxin mutant which is enzymatically inactive reduces their ability to migrate into lymph nodes (Kanda, H., et al., *Autotaxin, an ectoenzyme that produces lysophatidic acid, promotes the entry of lymphocytes into secondary lymphoid organs*. Nat Immunol, 2008. 9(4): p. 415-23). Treatment of the T cells with the inhibitors developed by us can likewise block migration thereof into lymph nodes.

During an inflammation, T cells can also migrate into other body tissue and drive forward the inflammation reaction there, which can result in organ damage. It has been shown in an animal model that blood vessels in inflamed tissue begin to express autotaxin [(Nakasaki, T., et al., *Involvement of the lysophosphatidic acid-generating enzyme autotaxin in lymphocyte-endothelial cell interactions*. Am J Pathol, 2008. 173 (5): p. 1566-76). It can therefore be assumed that autotaxin is also able to control the migration of T cells into body tissue during an inflammation. Increased autotaxin production is indeed also evident in humans both in inflamed intestinal tissue in the case of chronic inflammatory intestinal diseases (Wu, F., et al., *Genome-wide gene expression differences in Crohn's disease and ulcerative colitis from endoscopic pinch biopsies: insights into distinctive pathogenesis*. Inflamm Bowel Dis, 2007. 13(7): p. 807-21) and also in affected joints (Nochi, H., et al., *Stimulatory role of lysophosphatidic acid in cyclooxygenase-2 induction by synovial fluid of patients with rheumatoid arthritis in fibroblast-like synovial cells*. J Immunol, 2008. 181(7): p. 5111-9.) and synovial fibroblasts (Kehlen, A., et al., *IL-1 beta-and IL-4-induced down-regulation of autotaxin mRNA and PC-1 in fibroblast-like synoviocytes of patients with rheumatoid arthritis (RA)*. Clin Exp Immunol, 2001. 123(1): p. 147-54.) of arthritis patients. Since the migration of T cells into tissue plays a role in both inflammatory diseases, inhibition of autotaxin may suppress this process and thus have a positive influence on the course of the disease.

Surprisingly, it has been found that the compounds according to the invention cause specific inhibition of the enzyme family of the nucleotides pyrophosphatases and phosphodiesterases, in particular autotaxin. The compounds according to the invention preferably exhibit an advantageous biological activity, which can easily be detected in the assays described, for example, herein. In assays of this type, the compounds according to the invention preferably exhibit and cause an inhibiting effect, which is usually documented by $IC_{50}$ values in a suitable range, preferably in the micromolar range and more preferably in the nanomolar range.

In general, all solid and non-solid tumours can be treated with the compounds of the formulae Ia to Im, such as, for example, monocytic leukaemia, brain, urogenital, lymphatic system, stomach, laryngeal and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of one or more nucleotides pyrophosphatases and/or phosphodiesterases, in particular autotaxin.

The present invention therefore relates to compounds according to the invention as medicaments and/or medicament active compounds in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such an administration.

It can be shown that the compounds according to the invention have an advantageous action in a xenotransplant tumour model.

The host or patient can belong to any mammalian species, for example a primate species, in particular humans; rodents, including mice, rats and hamsters; rabbits; horses, cattle, dogs, cats, etc. Animal models are of interest for experimental investigations, where they provide a model for the treatment of a human disease.

The sensitivity of a certain cell to treatment with the compounds according to the invention can be determined by testing in vitro. Typically, a culture of the cell is combined with a compound according to the invention at various concentrations for a time which is sufficient to enable the active agents to induce cell death or to inhibit migration, usually between approximately one hour and one week. For testing in vitro, cultivated cells from a biopsy sample can be used. The viable cells remaining after the treatment are then counted.

The dose varies depending on the specific compound used, the specific disease, the patient status, etc. Typically, a therapeutic dose is sufficient considerably to reduce the undesired cell population in the target tissue, while the viability of the patient is maintained. The treatment is generally continued until a considerable reduction has occurred, for example at least about a 50% reduction in the cell burden, and can be continued until essentially no undesired cells can be detected in the body.

PRIOR ART

Other sulfoxides which are capable of the inhibition of autotaxin are described in WO2009046841.

Other heterocyclic derivatives are described in WO 2002085352, WO 2002030422, EP 1002535, WO 9818793, EP 385848, FR 2637286, WO 2005097782, EP 709384, EP 396282, EP 49203.

SUMMARY OF THE INVENTION

The invention relates to the compounds of the formulae Ia to Im:

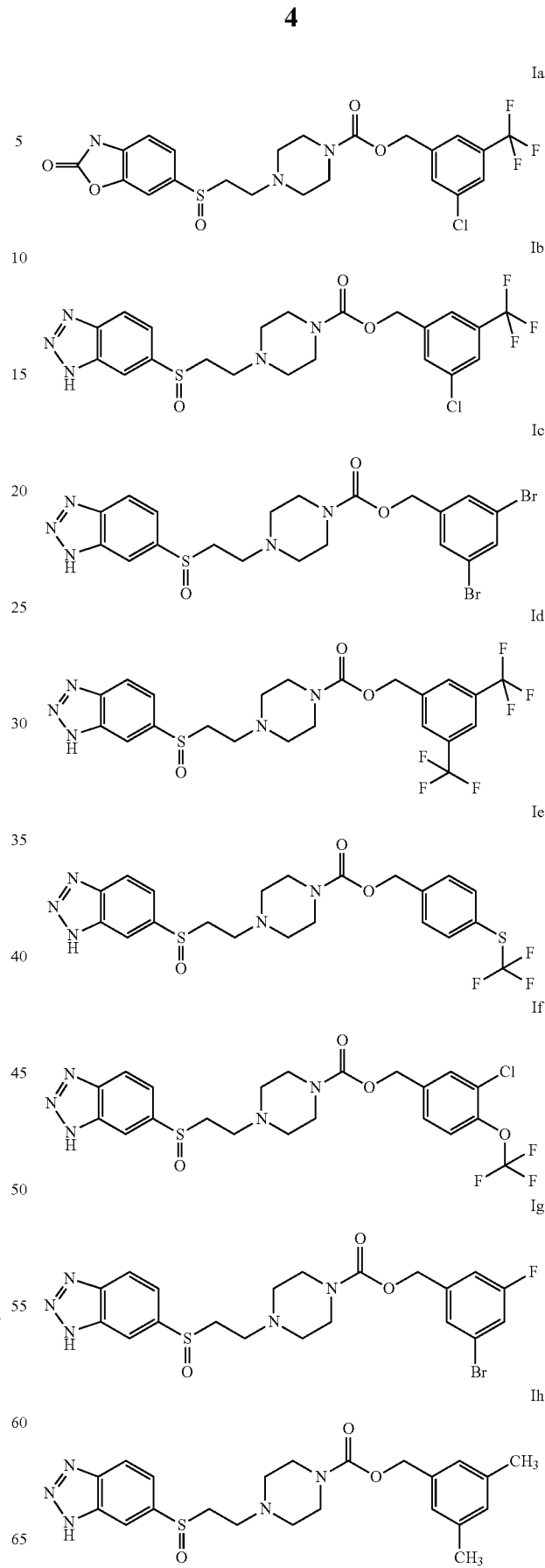

-continued

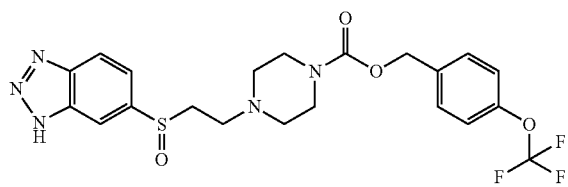
Ii

The invention also relates to the optically active forms (stereoisomers), the enantiomers and tautomers as described below, the racemates, the diastereomers and the salts, hydrates and solvates of these compounds. Solvates of the compounds are taken to mean adductions of inert solvent molecules onto the compounds which form owing to their mutual attractive force. Solvates are, for example, mono- or dihydrates or alcoholates.

The sulfoxides can also be depicted as dipolar resonance formulae. The sulfur arises therefrom as centre of chirality, and enantiomers are thus present:

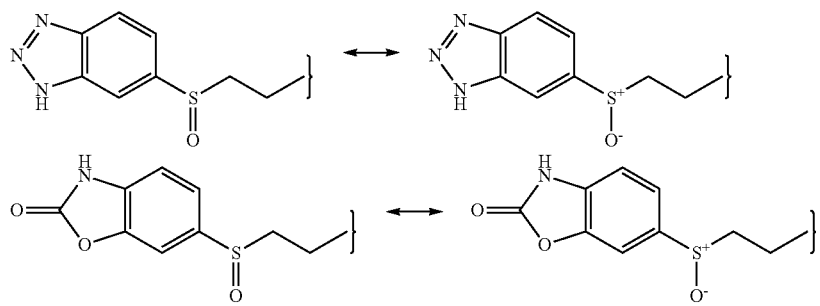

-continued

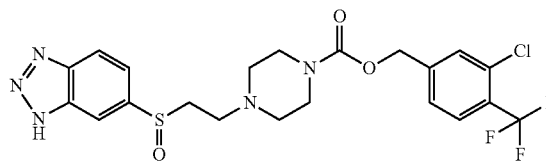
Ij tautomers:

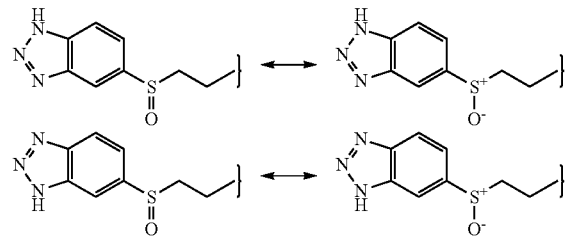

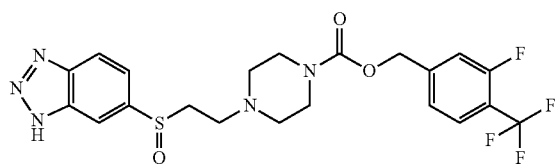
Ik

Il

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

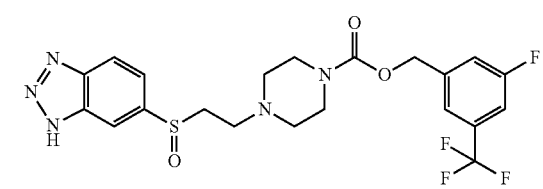
Im

The invention also relates to the use of mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The compounds of the formula Ia to Im and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

If desired, the starting materials can also be formed in situ, so that they are not isolated from the reaction mixture, but instead are immediately converted further into the compounds Ia to Im according to the invention.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds Ia to Im are for the most part prepared by conventional methods. If the compound of the formula Ia to Im contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds Ia to Im are likewise included. In the case of certain compounds of the formula Ia to Im, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds Ia to Im which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di(($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formulae Ia to Im are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formulae Ia to Im are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formulae Ia to Im in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formulae Ia to Im and/or pharmaceutically usable [lacuna] and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or drypressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formulae Ia to Im and salts and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula Ia to Im and the salts and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formulae Ia to Im depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formulae Ia to Im and/or pharmaceutically usable derivatives, salts, solvates, enantiomers, tautomers and stereoisomers thereof, including mixtures thereof in all ratios, and at least one further medicament active compound.

The invention also relates to a set (kit) consisting of separate packs of
(a) an effective amount of a compound of the formulae Ia to Im and/or pharmaceutically usable [lacuna] and stereoisomers thereof, including mixtures thereof in all ratios, and
(b) an effective amount of a further medicament active compound.

The set comprises suitable containers, such as boxes, individual bottles, bags or ampoules. The set may, for example, comprise separate ampoules, each containing an effective amount of a compound of the formulae Ia to Im and/or pharmaceutically usable [lacuna] and stereoisomers thereof, including mixtures thereof in all ratios, and an effective amount of a further medicament active compound in dissolved or lyophilised form.

The compounds Ia-Im are preferably employed for the treatment of tumour diseases, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenstrom's macroglobulinaemia and heavy chain disease.

The compounds of the formulae Ia to Im are preferably combined with the with known anti-cancer agents:

These known anti-cancer agents include the following: oestrogen receptor modulators, androgen receptor modulators, retinoid receptor modulators, cytotoxic agents, antiproliferative agents, prenyl protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxy-benzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate, but this is not intended to represent a restriction.

"Retinoid receptor modulators" refers to compounds which interfere with or inhibit the binding of retinoids to the receptor, regardless of mechanism.

Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or which inhibit or interfere with cell myosis, including alkylating agents, tumour necrosis factors, intercalators, microtubulin inhibitors and topoisomerase inhibitors.

Examples of cytotoxic agents include tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis-[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplastone, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyl-daunorubicin (see WO 00/50032), but this is not intended to represent a restriction.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]guinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)-ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methyl-amino]ethyl]-5-[4-hydroxy-3,5-dimethoxyphenyl]-5,5a,6,8,8a,9-hexohydro-furo(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-amino-ethyl)amino]benzo[g]isoguinoline-5,10-dione, 5-(3-aminopropylamino)-7,10-dihydroxy-2-(2-hydroxyethylaminomethyl)-6H- pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides, such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyrano-syl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those already listed under "angiogenesis inhibitors", such as trastuzumab, and tumour suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumour diseases.

The tumour is preferably selected from the group of tumours of the squamous epithelium, of the bladder, of the stomach, of the kidneys, of head and neck, of the oesophagus, of the cervix, of the thyroid, of the intestine, of the liver, of the brain, of the prostate, of the urogenital tract, of the lymphatic system, of the stomach, of the larynx and/or of the lung.

The tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

In another aspect, the invention encompasses a [lacuna] for the treatment of a patient who has a neoplasm, such as a cancer, by administration of a compound of the formula Ia to Im in combination with an antiproliferative agent. Suitable antiproliferative agents encompass those provided in Table 1.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS):
EI (electron impact ionisation) $M^{30}$
FAB (fast atom bombardment) $(M+H)^+$
ESI (electrospray ionisation) $(M+H)^+$
APCI-MS (atmospheric pressure chemical ionisation—mass spectrometry) $(M+H)^+$
LC/MS Method:
Solvent A: water+0.1% of TFA
Solvent B: acetonitrile+0.1% of TFA
Flow: 2.4 ml/min
Gradient:
0.0 min 4% of B
2.6 min 100% of B
Column: Chromolith Speed ROD RP-18e 50-4, 6 mm The following substances have been synthesised and characterised. However, the preparation and characterisation of the substances can also be carried out by the person skilled in the art in other ways.

EXAMPLE 1

Synthesis of 3,5-difluoromethylbenzyl 4-[2-(3H-benzotriazole-5-(R)sulfinyl)-ethyl]piperazine-1-carboxylate 10a

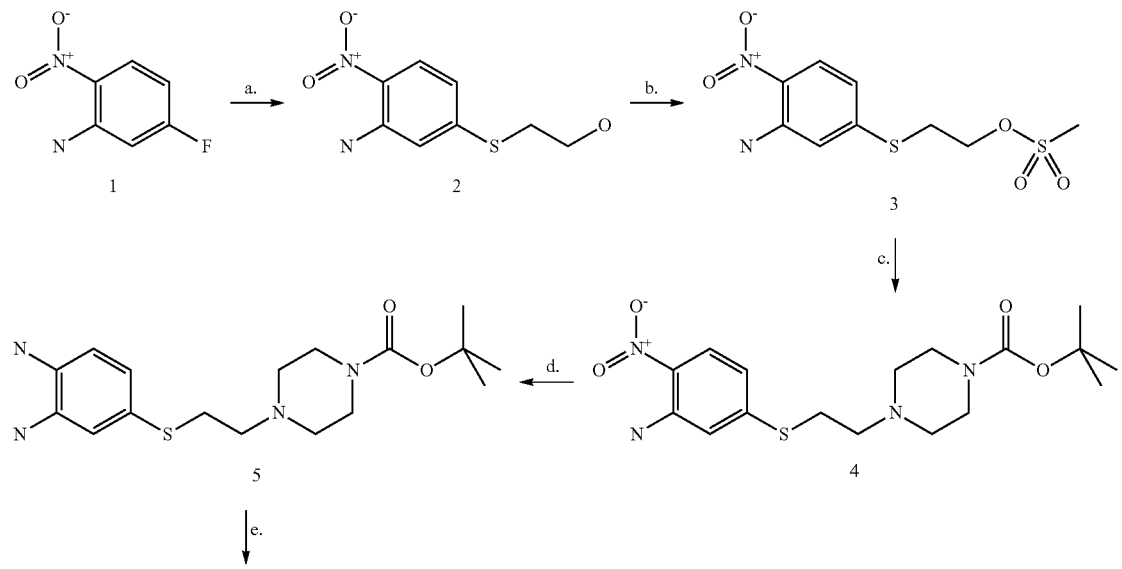

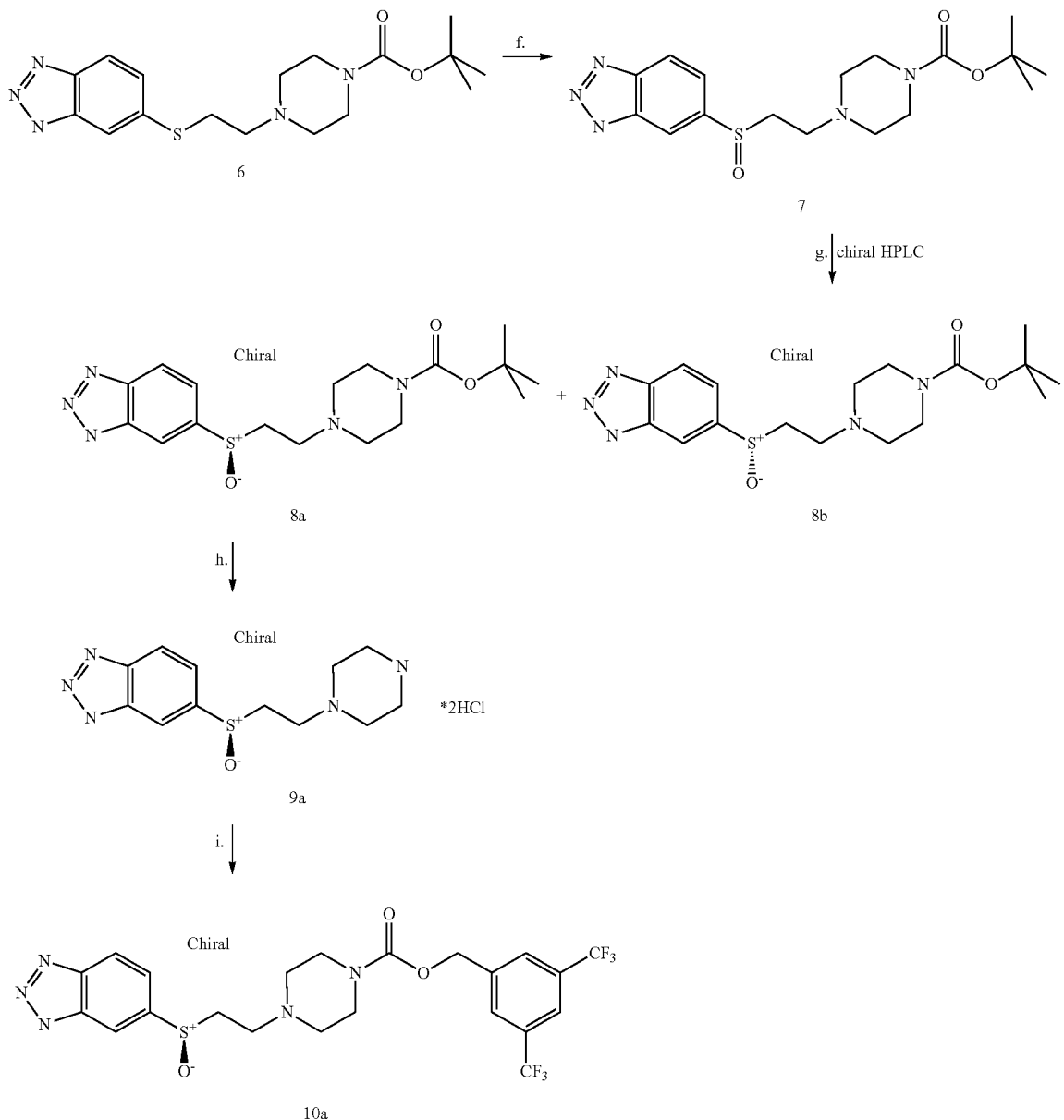

a. 5-Fluoro-2-nitrophenylamine 1 (33.6 g, 213 mmol, 90%) and caesium carbonate (77.1 g, 237 mmol) are suspended in 400 ml of acetonitrile (reddish suspension). 2-Mercaptoethanol (18.5 g, 237 mmol) are added to this suspension at RT, during which the reaction mixture immediately changes colour to yellow. The mixture is subsequently stirred at 60° C. for 18 h. The mixture is filtered, the residue is rinsed with acetonitrile, and the filtrate is evaporated to dryness, giving a yellowish-orange solid, which proved to be compound 2 and is reacted further without further purification.

b. Compound 2 (45.5 g, 212 mmol) is suspended in 250 ml of acetonitrile. Triethylamine (22.6 g, 223 mmol) is added to this deep-red suspension at RT, and the mixture is subsequently stirred at RT for 30 min. Methanesulfonyl chloride (25.5 g, 223 mmol) as a solution in 20 ml of dichloromethane is slowly added dropwise at RT (exothermic reaction), and stirring is subsequently continued at RT for 3 h, during which the product precipitates out as a yellow precipitate. The mixture is cooled in ice for 2 h, the yellow precipitate is filtered off and rinsed with copious acetonitrile. Filtrate and wash liquor are combined and evaporated. The concentrated solution is then likewise cooled, and further product is precipitated using double the amount of methyl tert-butyl ether. This is likewise filtered off and rinsed with acetonitrile. The two filter residues are combined and dried in vacuo, giving a yellow solid of compound 3, which is reacted further without further purification.

c. Compound 3 (61.9 g, 212 mmol) and Boc-piperazine (47.0 g, 250 mmol) are suspended in 400 ml of THF. A solution of 25.7 g (254 mmol) of triethylamine in 20 ml of THF is slowly added dropwise to this yellow suspension.

When the addition is complete, the mixture is stirred at 70° C. for 15 h. The resultant precipitate is filtered off, washed with THF and discarded. The filtrate and wash liquor is combined and evaporated to dryness. This residue is taken up in ethyl acetate, washed a number of times with water and with NaCl solution, dried using sodium sulfate, filtered and evaporated to dryness. The yellow product 4 is reacted further without further purification.

d. Compound 4 (40.1 g, 105 mmol) is dissolved in 540 ml of THF, sponge nickel catalyst (water-wet, 10 g) is added, and the mixture is shaken at RT for 15 h at hydrogen atmospheric pressure. A further 10 g of the catalyst are added, and the mixture is shaken for a further 17 h in a hydrogen atmosphere. The catalyst is filtered off, and the filtrate is evaporated to dryness. This black oily residue is taken up in ethyl acetate, washed three times with water and once with NaCl solution, dried using sodium sulfate, filtered and evaporated in a rotary evaporator. The dark-red oil of compound 5 is processed further without further purification.

e. Compound 5 (32.5 g, 92.2 mmol) is dissolved in glacial acetic acid (320 ml), and sodium nitrite (6.4 g, 92.8 mmol) is added. The mixture is stirred at RT for 2 h. The mixture is then diluted with water, and the reaction solution is extracted a number of times with ethyl acetate. The org. phase is washed with NaHCO3 solution and NaCl solution, dried using Na2SO4, filtered and evaporated to dryness. The dark resinous oil of compound 6 is processed further without further purification.

f. Compound 6 (27.1 g, 74.5 mmol) is dissolved in 320 ml of glacial acetic acid, and 15.5 ml of hydrogen peroxide (30% in water) are added dropwise with stirring. The mixture is stirred at RT for 15 h, diluted with water and ethyl acetate and then neutralised with stirring firstly using solid NaHCO3 then using NaHCO3 solution. The organic phase is isolated and washed with water and with NaCl solution, dried using sodium sulfate, filtered and evaporated to dryness. The dark amorphous crystallisate is identified as compound 7 and is separated into the enantiomers without further purification.

g. Compound 7 (21.0 g, 44.3 mmol) is dissolved in 250 ml of methanol. The solution is separated by preparative SFC (8 ml per injection) via a Chiralpak AD-H 3×20 cm 5 µm column and CO2 (80 ml) and methanol (16 ml). 2 fractions are collected and are each evaporated to dryness. Fraction 1 contains 6.9 g (18.2 mmol, 41%) of a colourless solid, which is randomly assigned to the absolute structure 8b. Structure 8a is assigned to the colourless solid of fraction 2.

h. The enantiomerically pure compound 8a (7.00 g, 18.4 mmol) is dissolved in 80 ml of isopropanol, 80 ml of 5-6 N HCl in isopropanol are added at RT with stirring, and the mixture is stirred at RT for a further 15 h. The mixture is evaporated to dryness in vacuo, dissolved in a little dioxane, water is admixed, the mixture is frozen and lyophilised, giving a colourless solid of high purity which can be assigned to compound 9a as the dihydrochloride. The material is used further without further purification.

i. Compound 9a (175 mg, 0.50 mmol) is dissolved in 2 ml of DMF, and triethylamine 151 µl, 1.09 mmol) is added. 3,5-Bistrifluoromethylbenzyl alcohol (124 mg, 0.50 mmol, 98%) and 1,1'-carbonyldiimidazole (80.6 mg, 0.50 mmol) are weighed out into a separate vessel, dissolved in 3 ml of DMF and stirred at RT for one hour. The previously prepared solution of compound 9a is added to this mixture, and the entire solution is stirred at RT overnight. The mixture is evaporated to dryness, the residue is taken up in dichloromethane, washed with water and NaCl solution, dried using sodium sulfate, filtered and again evaporated to dryness. The residue is purified by column chromatography (ethyl acetate/MeOH), giving compound 10a as colourless solid.

Enantiomer 8b can also be converted into the corresponding antipode of compound 10a analogously to procedures h. and i. described.

Racemate 7 can likewise be converted into the racemic mixture of 10a via procedures h. and i. The separation into the antipodes can also be carried out at this stage analogously to g.

EXAMPLE 2

Synthesis of 3-chloro-5-trifluoromethylbenzyl 4-[2-(2-oxo-2,3.dihydro-benzoxazolyl-6(R)-sulfinyl)ethyl]piperazine-1-carboxylate 20a

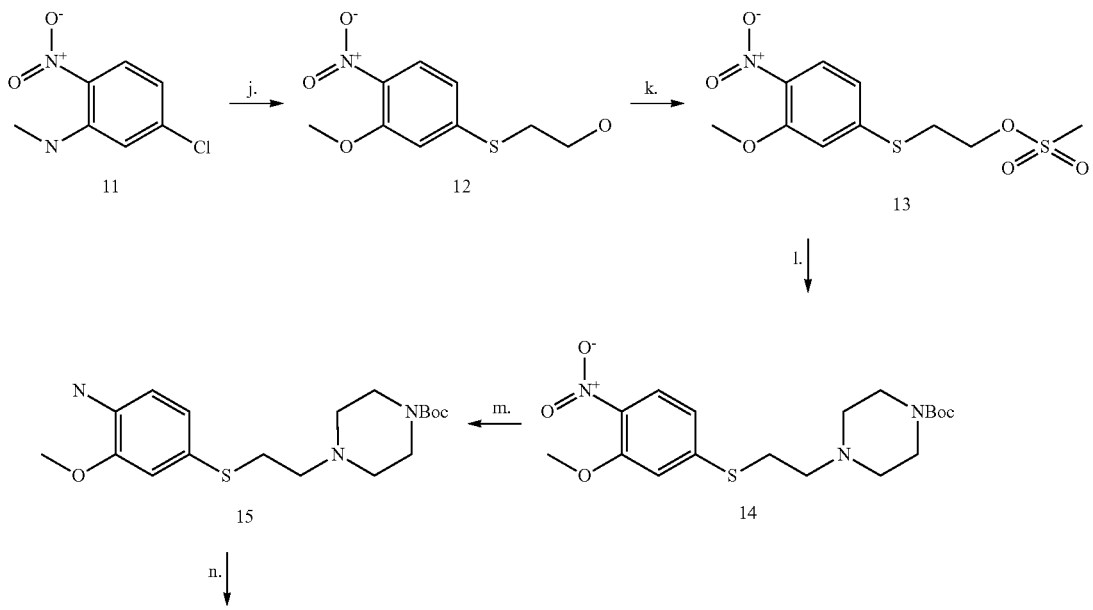

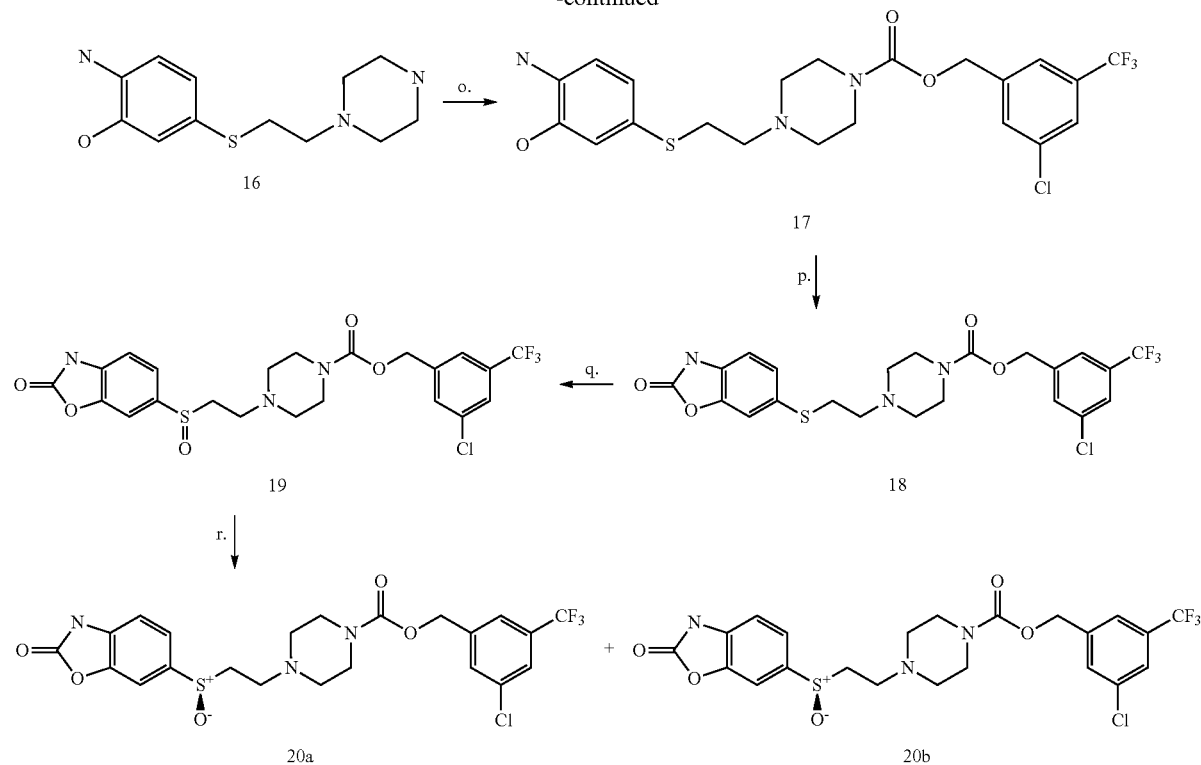

j. 5-Chloro-2-nitroanisole (48.3 g, 0.25 mol) is dissolved in 300 ml of acetonitrile. A solution of 2-mercaptoethanol (17.8 ml, 0.25 mol) in 100 ml of acetonitrile and potassium carbonate (69.1 g, 0.5 mol) is added with stirring, and the mixture is stirred under reflux overnight. The reaction mixture is cooled, 500 ml of ice-water are added, and the mixture is then extracted twice with 400 ml of ethyl acetate. The organic phase is washed with 0.2 N NaOH solution and then with water, dried over magnesium sulfate, filtered and evaporated in a rotary evaporator. Crystallisation using diethyl ether gives beige crystals of compound 12.

k. Compound 12 (48.0 g, 0.209 mol) is suspended in 50 ml of dichloromethane, and triethylamine (19 ml, 0.209 mol) is added. Methanesulfonyl chloride (16.2 ml, 0.209 mol) is added dropwise with stirring at a maximum internal temperature of 15° C. The mixture is stirred at room temperature for a further hour, the reaction mixture is then added to 300 ml of ice-water and extracted twice with 200 ml of dichloromethane. The organic phase is dried using magnesium sulfate, filtered and evaporated in a rotary evaporator, giving compound 13 as oily residue.

l. Compound 13 (57 g, 0.185 mol), tert-butyl piperazine-1-carboxylate (34.5 g, 0.185 mol), and caesium carbonate (60.1 g, 0.185 mol) are dissolved in 300 ml of acetonitrile and stirred at 60° C. overnight. 400 ml of water and 400 ml of dichloromethane are added, and the organic phase is separated off. It is dried using magnesium sulfate, filtered and evaporated in a rotary evaporator. The residue is purified over a silica-gel column with ethyl acetate as eluent, giving compound 14 as amorphous solid substance.

m. 3.15 g of 5% Pd/C are added to compound 14 (6.3 g, 15.8 mmol) in 85 ml of tetrahydrofuran. And hydrogenated at room temperature for 16 hours. The catalyst is filtered off. Evaporation of the solution gives compound 15 as solid substance.

n. Compound 15 (5.5 g 0.015 mol) are dissolved in 70 ml of 47% hydrobromic acid and stirred at 150° C. for 8 hours. The reaction mixture is then allowed to cool, and the deposited crystals are filtered off with suction. They are washed with a little water and dried, giving compound 16.

o. Compound 16 (1.18 g, 3.0 mmol), 1,1-carbonyldiimidazole (0.486 g, 3.0 mmol) 3-chloro-5-trifluoromethylbenzyl alcohol (0.63 g, 3.0 mmol) and triethylamine (0.42 ml, 3.0 mmol) are dissolved in 20 ml of DMF and stirred at RT overnight. The reaction mixture is evaporated and taken up in 50 ml of water and 100 ml of ethyl acetate. The organic phase is separated off, dried using magnesium sulfate, filtered and evaporated in a rotary evaporator. The residue is purified over a silica-gel column with ethyl acetate as eluent, giving compound 17 as solid substance.

p. Compound 17 (0.8 g, 1.63 mmol) and 1,1-carbonyldiimidazole (0.265 g, 1.63 mmol) are stirred at RT for 3 hours in 10 ml of THF. 100 ml of water are then added to the batch, which is then extracted twice with 100 ml of ethyl acetate. The organic phase is dried using magnesium sulfate, filtered and evaporated in a rotary evaporator. Crystallisation using ethanol gives compound 18 as pale-brown crystals.

q. Compound 18 (0.72 g, 1.4 mmol) is dissolved in 8 ml of glacial acetic acid. Hydrogen peroxide (30% in water, 0.29 ml 2.8 mmol) is then added, and the mixture is stirred at RT for 3 hours. The batch is then added to 100 ml of ice-water and neutralised using saturated NaHCO3 solution. The mixture is extracted twice with 50 ml of ethyl acetate. The organic phase is dried using magnesium sulfate, filtered and evaporated in a rotary evaporator. Crystallisation using ethanol gives compound 19 as pale crystals.

r. Racemate 19 (0.35 g, 0.66 mmol) is separated by means of preparative HPLC on a Chiralpak AD (5×40 cm, 20 μm) with methanol/ethanol (25/75) (flow rate: 100 ml/min), giving the two enantiomers 20a and 20b as amorphous solid substance.

The following compounds can be prepared in an analogous manner as described in Examples 1 and 2:

3-chloro-5-trifluoromethylbenzyl 4-[2-(2-oxo-2,3-dihydrobenzooxazole-6(R)-sulfinyl)ethyl]piperazine-1-carboxylate (Ia)

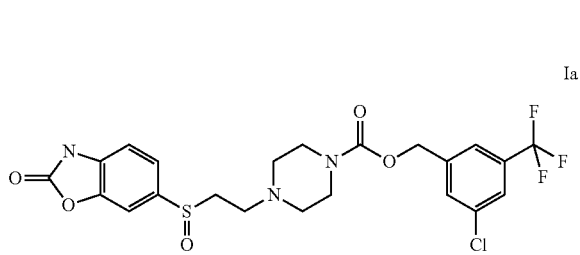 [SMILES: O=C(OCc1cc(Cl)cc(C(F)(F)F)c1)N1CCN(CCS(=O)c2ccc3[nH]c(=O)oc3c2)CC1]

racemate: 1H NMR (500 MHz, DMSO) δ=12.02 (m, <1H), 7.81 (s, 1H), 7.75 (s, 1H), 7.69 (s, 1H), 7.62 (d, J=1.5, 1H), 7.47 (dd, J=8.1, 1.5, 1H), 7.25 (d, J=8.1, 1H), 5.15 (s, 2H), 4.45-3.30 (m, 4H), 3.14-3.07 (m, 1H), 3.00-2.90 (m, 1H), 2.75-2.68 (m, 1H), 2.47-2.27 (m, 5H), Rt[min] 1.80, 3-chloro-5-trifluoromethylbenzyl 4-[2-(3H-benzotriazole-5(R)-sulfinyl)ethyl]-piperazine-1-carboxylate (Ib)

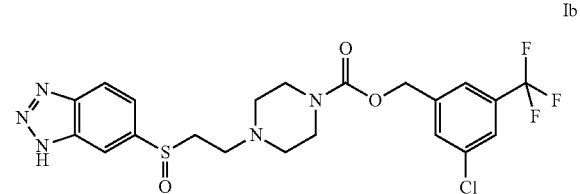 [SMILES: O=C(OCc1cc(Cl)cc(C(F)(F)F)c1)N1CCN(CCS(=O)c2ccc3nn[nH]c3c2)CC1]

1H NMR (400 MHz, DMSO) δ15.87 (s, 1H), 8.24 (s, 1H), 8.09 (d, J=8.7, 1H), 7.82 (s, 1H), 7.78-7.67 (m, 3H), 5.15 (s, 2H), 3.55-3.14 (m, 5H), 3.07-2.91 (m, 1H), 2.81-2.72 (1H), 2.48-2.28 (m, 5H), Rt[min] 1.79, 3,5-dibromobenzyl 4-[2-(3H-benzotriazole-5(R)-sulfinyl)ethyl]piperazine-1-carboxylate (Ic)

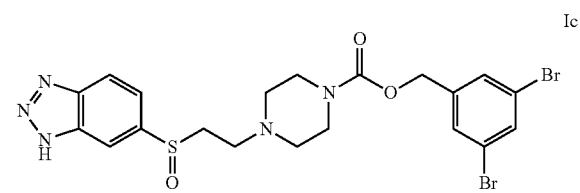 [SMILES: O=C(OCc1cc(Br)cc(Br)c1)N1CCN(CCS(=O)c2ccc3nn[nH]c3c2)CC1]

1H NMR (500 MHz, DMSO) δ=16.03 (s, 1H), 8.25 (s, 1H), 8.10 (d, J=8.6, 1H), 7.79 (t, J=1.6, 1H), 7.74 (d, J=8.5, 1H), 7.58 (d, J=1.6, 2H), 5.06 (s, 2H), 3.52-3.17 (m, 5H), 3.06-2.96 (m, 1H), 2.81-2.74 (m, 1H), 2.50-2.28 (m, 5H), Rt[min] 1.76, 3,5-bistrifluoromethylbenzyl 4-[2-(3H-benzotriazole-5(S)-sulfinyl)ethyl]-piperazine-1-carboxylate (Id)

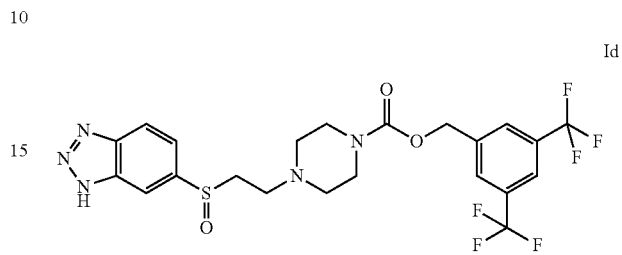

1H NMR (400 MHz, DMSO) δ=15.98 (s, 1H), 8.25 (s, 1H), 8.15-8.00 (m, 4H), 7.74 (d, J=8.6, 1H), 5.25 (s, 2H), 3.40-3.14 (m, 5H), 3.10-2.92 (m, 1H), 2.85-2.68 (m, 1H), 2.49-2.24 (m, 5H), Rt[min] 1.85, 4-trifluoromethylsulfanylbenzyl 4-[2-(3H-benzotriazole-5(R)-sulfinyl)ethyl]-piperazine-1-carboxylate (Ie)

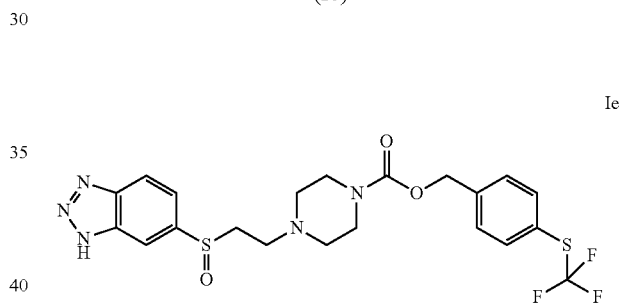

1H NMR (400 MHz, DMSO) δ=16.02 (s, 1H), 8.25 (s, 1H), 8.10 (d, J=8.6, 1H), 7.76-7.70 (m, 3H), 7.50 (d, J=8.3, 2H), 5.14 (m, 2H), 3.47-3.15 (m, 5H), 3.08-2.94 (m, 1H), 2.81-2.72 (m, 1H), 2.48-2.27 (m, 5H), Rt[min] 1.85, 3-chloro-4-trifluoromethoxybenzyl 4-[2-(3H-benzotriazole-5(R)-sulfinyl)-ethyl]piperazine-1-carboxylate (If)

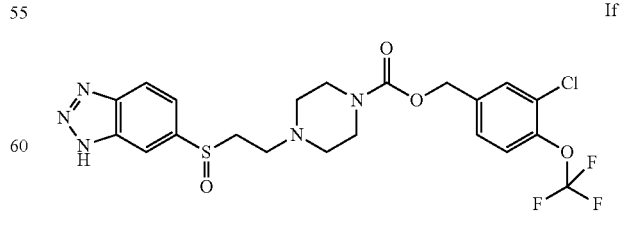

1H NMR (500 MHz, DMSO) δ=16.08 (s, 1H), 8.24 (s, 1H), 8.09 (d, J=8.6, 1H), 7.73 (dd, J=8.6, 1.1, 1H), 7.67 (d, J=2.0, 1H), 7.57 (dd, J=8.6, 1.1, 1H), 7.45 (dd, J=8.5, 2.0, 1H), 5.07

(s, 2H), 3.35-3.15 (m, 5H), 3.07-2.95 (m, 1H), 2.80-2.72 (m, 1H), 2.48-2.30 (m, 5H), Rt[min] 1.80, 3-bromo-5-fluoromethylbenzyl 4-[2-(2-oxo-2,3-dihydrobenzooxazole-6(R)-sulfinyl)ethyl]piperazine-1-carboxylate

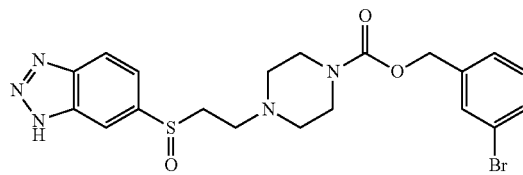

Ig

1H NMR (500 MHz, DMSO) δ=16.10 (s, 1H), 8.25 (s, 1H), 8.10 (d, J=8.6, 1H), 7.74 (d, J=8.6, 1H), 7.55-7.46 (m, 1H), 7.42 (s, 1H), 7.24 (d, J=9.2, 1H), 5.08 (s, 2H), 3.32-3.14 (m, 5H), 3.09-2.94 (m, 1H), 2.81-2.74 (m, 1H), 2.50-2.27 (m, 5H), Rt[min] 1.63, 3,5-dimethylbenzyl 4-[2-(3H-benzotriazole-5(R)-sulfinyl)ethyl]piperazine-1-carboxylate (Ih)

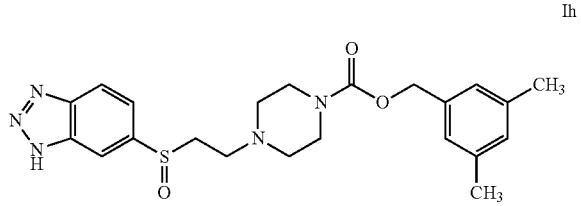 [SMILES: Cc1cc(C)cc(COC(=O)N2CCN(CCS(=O)c3ccc4nn[nH]c4c3)CC2)c1]

Ih

1H NMR (500 MHz, DMSO) δ=15.91 (s, 1H), 8.24 (s, 1H), 8.09 (d, J=8.6, 1H), 7.73 (dd, J=8.6, 1.1, 1H), 6.93 (s, 3H), 4.97 (s, 2H), 3.35-3.13 (m, 5H), 3.07-2.93 (m, 1H), 2.80-2.71 (m, 1H), 2.50-2.29 (m, 6H), 2.25 (s, 5H), Rt[min] 1.62, 4-trifluoromethoxybenzyl 4-[2-(3H-benzotriazole-5(R)-sulfinyl)ethyl]-piperazine-1-carboxylate (Ii)

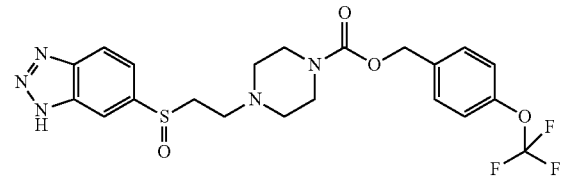

Ii

1H NMR (400 MHz, DMSO) δ=15.99 (s, 1H), 8.24 (s, 1H), 8.09 (d, J=8.6, 1H), 7.79-7.69 (m, 1H), 7.48 (d, J=8.3, 2H), 7.36 (d, J=8.3, 2H), 5.09 (s, 2H), 3.29-3.14 (m, 5H), 3.08-2.94 (m, 1H), 2.82-2.70 (m, 1H), 2.49-2.25 (m, 5H), Rt[min] 1.62, 3-chloro-4-trifluoromethylbenzyl 4-[2-(3H-benzotriazole-5(R)-sulfinyl)ethyl]-piperazine-1-carboxylate (Ij)

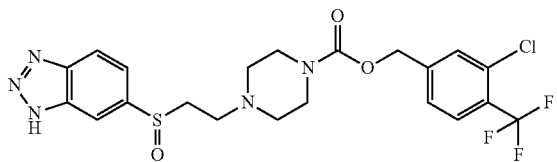

Ij

1H NMR (500 MHz, DMSO) δ=16.01 (s, 0.5H), 8.26 (s, 1H), 8.10 (d, J=8.6, 1H), 7.87 (d, J=8.1, 1H), 7.74 (d, J=8.6, 1H), 7.69 (s, 1H), 7.52 (d, J=8.1, 1H), 5.21 (m, 2H), 3.29-3.16 (m, 5H), 3.07-2.94 (m, 1H), 2.84-2.70 (m, 1H), 2.50-2.30 (m, 5H), Rt[min] 1.75, 3-fluoro-4-trifluoromethylbenzyl 4-[2-(3H-benzotriazole-5(R)-sulfinyl)ethyl]-piperazine-1-carboxylate

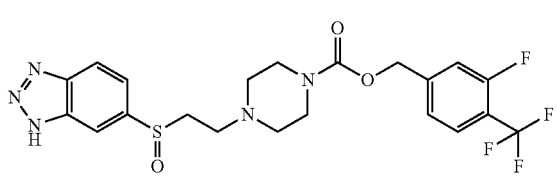

Ik

1H NMR (500 MHz, DMSO) δ=15.92 (m, 1H), 8.25 (s, 1H), 8.10 (d, J=8.6, 1H), 7.80 (t, J=7.8, 1H), 7.74 (d, J=8.7, 1H), 7.48 (d, J=11.8, 1H), 7.39 (d, J=8.0, 1H), 5.17 (s, 2H), 3.28-3.15 (m, 5H), 3.08-2.96 (m, 1H), 2.82-2.74 (m, 1H), 2.49-2.25 (m, 5H), Rt[min] 1.69, 1-{4-[2-(3H-benzotriazole-5(R)-sulfinyl)ethyl]piperazin-1-yl}-3-(4-trifluoro-methylphenyl)propan-1-one

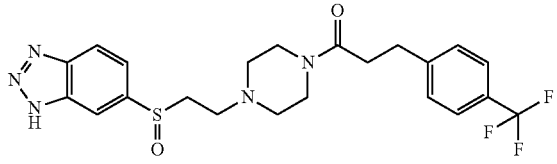

Il

1H NMR (500 MHz, DMSO) δ=≈20.00 (s, 1H), 8.25 (s, 1H), 8.10 (d, J=8.6, 1H), 7.74 (d, J=8.6, 1H), 7.62 (d, J=8.1, 2H), 7.47 (d, J=8.0, 2H), 3.30-3.10 (m, 5H), 3.06-2.96 (m,

1H), 2.89 (t, J=7.5, 2H), 2.78-2.70 (m, 1H), 2.65 (t, J=7.6, 2H), 2.48-2.38 (m, 1H), 2.37-2.18 (m, 4H), Rt[min] 1.64 and 3-fluoro-5-trifluoromethylbenzyl 4-[2-(2-oxo-2,3-dihydrobenzooxazole-6(R)-sulfinyl)ethyl]piperazine-1-carboxylate

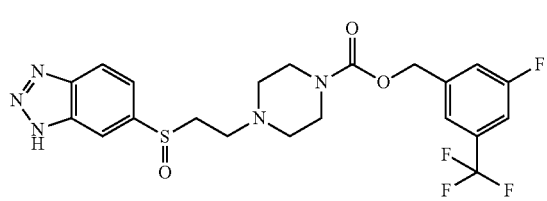

1H NMR (500 MHz, DMSO) δ=15.60 (s, 1H), 8.24 (s, 1H), 8.08 (d, J=8.6, 1H), 7.72 (d, J=8.7, 1H), 7.61 (d, J=8.6, 1H), 7.58-7.48 (m, 2H), 5.16 (s, 2H), 3.36-3.14 (m, 5H), 3.07-2.93 (m, 1H), 2.81-2.74 (m, 1H), 2.49-2.27 (m, 5H), Rt[min] 1.69.

EXAMPLE A

Autotaxin Test (Enzyme Test)

Test Description

The autotaxin activity is measured indirectly using Amplex Red reagent. Amplex Red is measured here as fluorogenic indicator for the $H_2O_2$ formed.

In detail, autotaxin converts the substrate lysophosphatidylcholine (LPC) into phosphocholine and lysophosphatidylic acid (LPA). After this conversion, the phosphocholine is reacted with alkaline phosphatase to give inorganic phosphate and choline. In the next step, choline is oxidised by choline oxidase to give betaine, with formation of $H_2O_2$. $H_2O_2$ reacts with Amplex Red reagent in the presence of peroxidase (horseradish peroxidase) in a 1:1 stoichiometry and forms the highly fluorescent resorufin. The fluorescence is measured in a reaction-dependent kinetic mode in order that fluorescent signals from possible other fluorescent substances which are not involved in the reaction can be corrected out.

Test Procedure 1.5 μl of a standard solution or of the test substances (substances with the name A(n)) in individual concentrations dissolved in 20 mM Hepes pH 7.2 with a maximum of 7.7% of DMSO are pre-incubated together with 10 μl (16 ng) of highly purified recombinant autotaxin in a black microtitre plate provided with 384 wells at 22° C. for 30 min. The reaction is then initiated by addition of 5 μl of L-α-lysophosphatidylcholine (LPC), where the final concentration of LPC is 75 μM. The mixture is incubated at 37° C. for 90 min. After the incubation, Amplex Red reagent, peroxidase (horseradish peroxidase) and choline oxidase is added, and the fluorescence is immediately measured at 612 nm with excitation of 485 nm in a "Tecan Ultra multimode" reader. The activity of autotaxin is calculated indirectly via detection of the $H_2O_2$ formed.

| Material: | |
|---|---|
| Microtitre plate: | PS microplate, 384 wells, small volume, black Corning, Cat#3677 |

-continued

| Material: | |
|---|---|
| Protein: | recombinant autotaxin (Baculovirale Hi5 Expression) |
| Substrate: | L-α-lysophosphatidylcholine (chicken egg)); Avanti Polar Lipids # 830071P |
| Standard: | C14 LPA, Avanti Polar Lipids, Cat# 857120P |
| Detection reagent: | Amplex Red reagent; Invitrogen # A12222; dissolved in 1.923 ml of DMSO peroxidase type VI-A (horseradish) from Sigma # P6782; dissolved in 7.45 ml of test buffer, choline oxidase; Sigma # C5896; dissolved in 2.47 ml of test buffer |
| Detection reagent mix: | 1:100 dilution of Amplex Red reagent in test buffer |
| Test buffer: | 200 mM Tris HCl, Merck, Cat # 1.08219, pH 7.9, 0.1% of BSA, lipid-free, Roche Cat#775835 |

The IC50 values of all compounds described are <1 μM in this assay.

The following examples relate to medicaments:

EXAMPLE B

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE C

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE D

Solution

A solution is prepared from 1 g of an active compound of the formula I, 9.38 g of $NaH_2PO_4 \cdot 2H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE E

Ointment 500 mg of an active compound of the formula I are mixed with 99.5 g of Vaseline under aseptic conditions.

EXAMPLE F

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE G

Dragees

Tablets are pressed analogously to Example E and subsequently coated in a conventional manner with a coating of sucrose, potato starch, talc, tragacanth and dye.

EXAMPLE H

Capsules 2 kg of active compound of the formula I are introduced into hard gelatine capsules in a conventional manner in such a way that each capsule contains 20 mg of the active compound.

EXAMPLE I

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

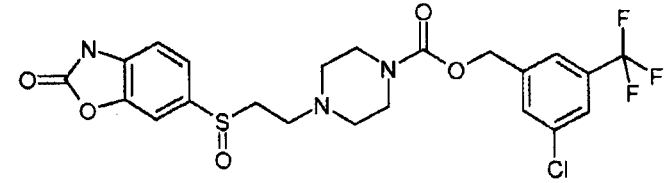

The invention claimed is:

1. A compound, which is one of the following compounds

Ia

Ib

Ic

Id

Ie

-continued

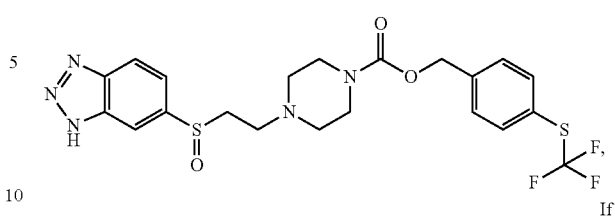

If

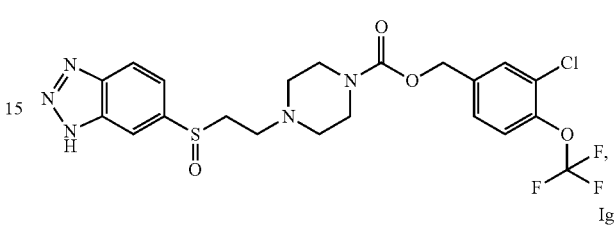

Ig

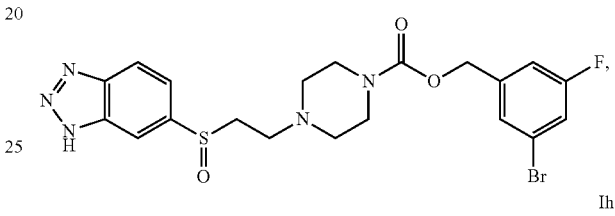

Ih

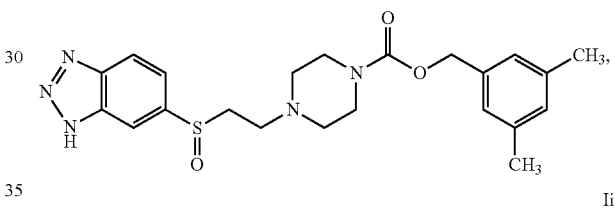

Ii

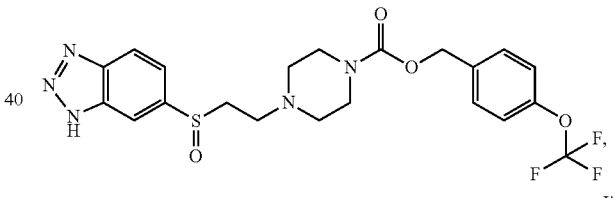

Ij

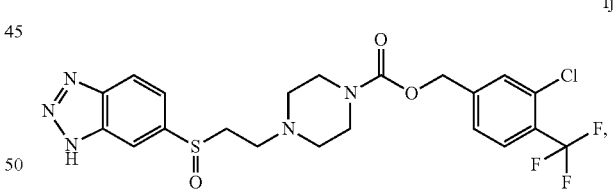

Ik

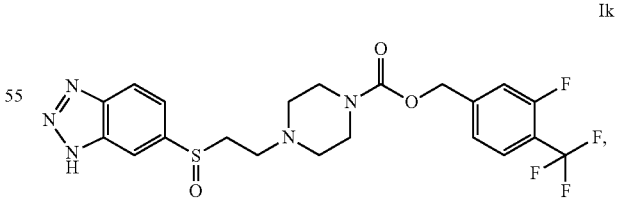

Il

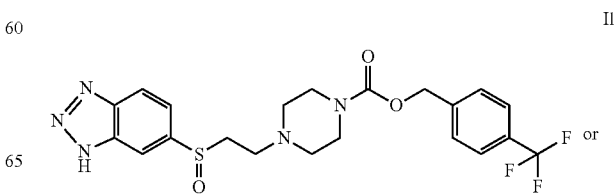

or or a pharmaceutically acceptable salt, enatiomer, tautomer or stereoisomer thereof.

2. A pharmaceutical composition, comprising at least one compound according to claim 1 or a pharmaceutically acceptable salt, enatiomer, tautomer or stereoisomer thereof, and a pharmaceutically acceptable carrier.

3. A method for treating a disease in which the inhibition, regulation and/or modulation of autotaxin plays a role, comprising administering to a subject in need thereof an effective amount of one of the following compounds

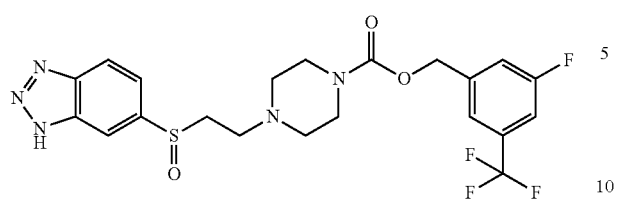
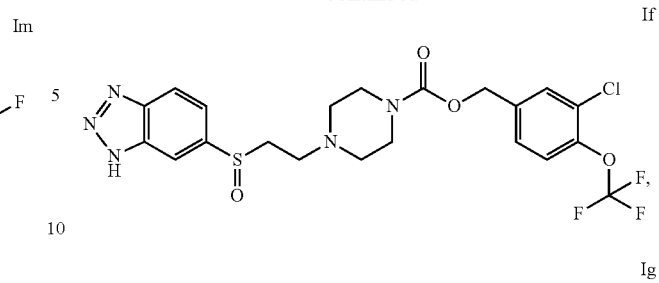
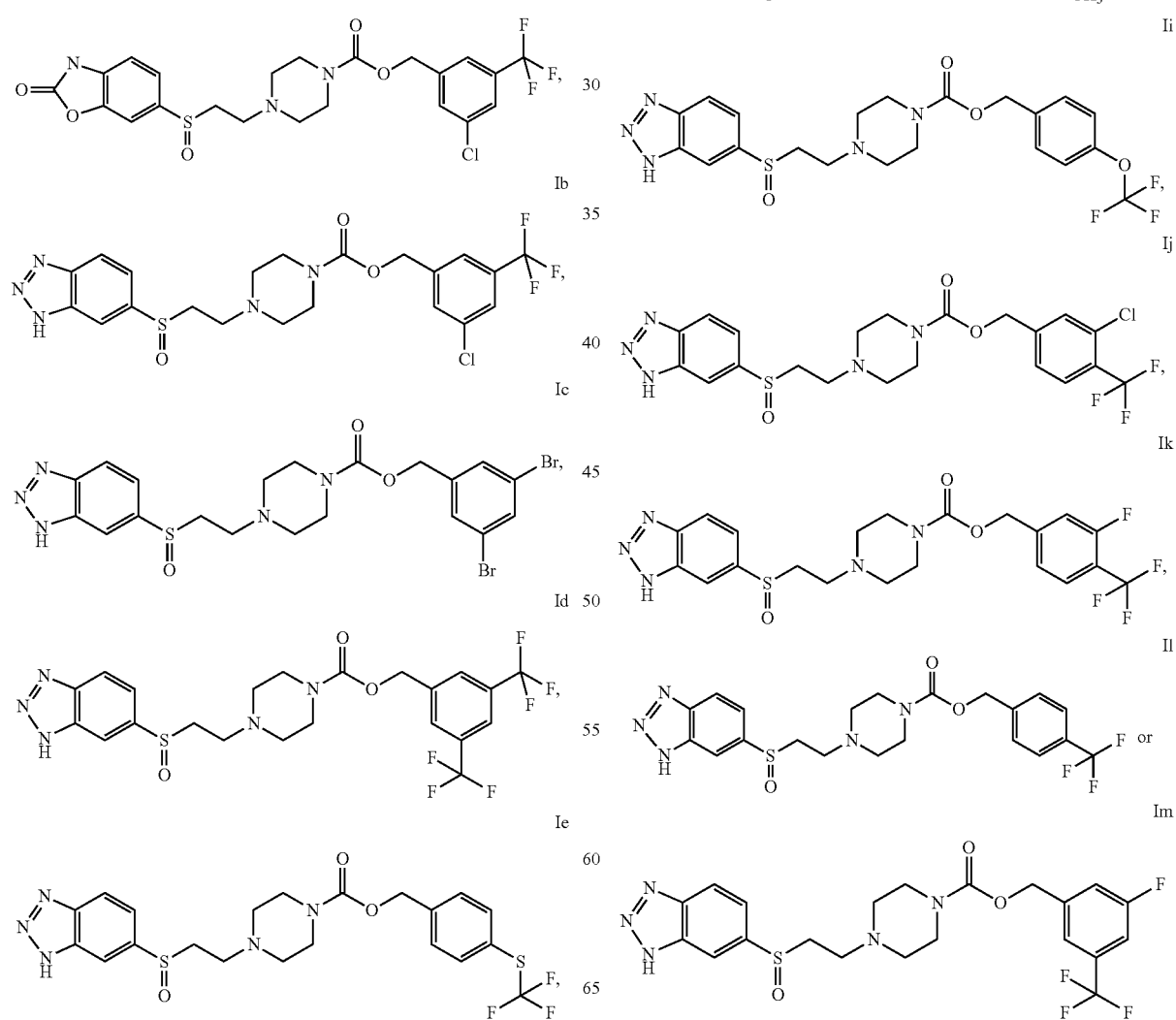

or a pharmaceutically acceptable salt, enatiomer, tautomer or stereoisomer thereof.

4. A method according to claim 3, wherein the disease is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carci-noma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligo-dendroglioma, meningioma, melanoma, neuroblastoma, retinoblastoma, leukaemia, lymphoma, multiple myeloma, Waldenstrom's macroglobulinaemia or heavy chain disease.

5. A pharmaceutical composition according to claim 2, further comprising at least one further pharmaceutically active compound.

6. A kit comprising separate packs of
(a) an effective amount of one of the following compounds

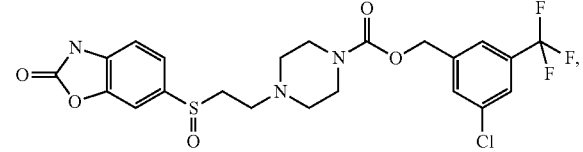

Ia

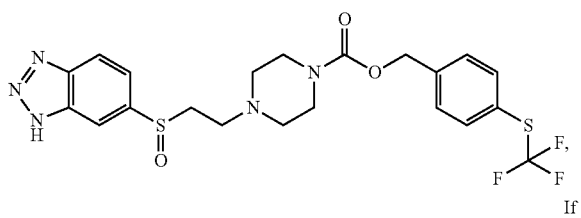

Ie

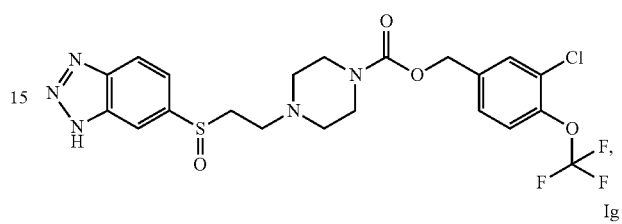

If

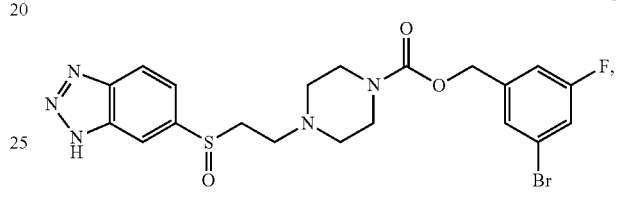

Ig

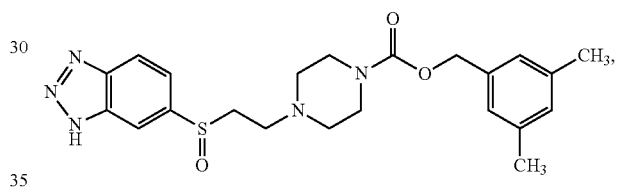

Ih

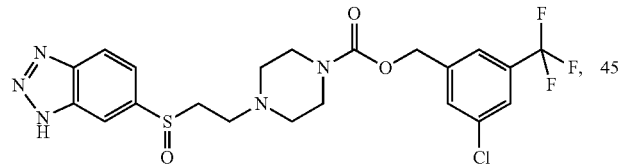

Ib

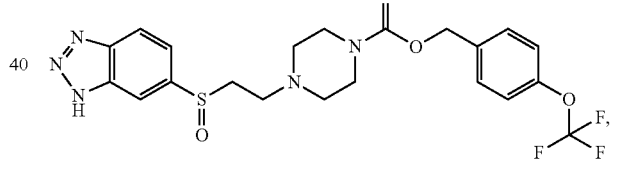

Ii

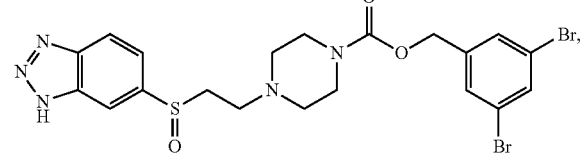

Ic

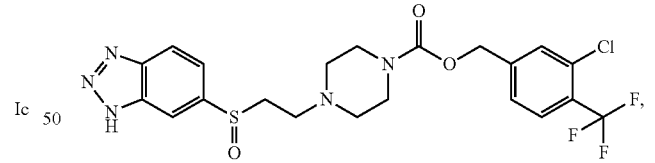

Ij

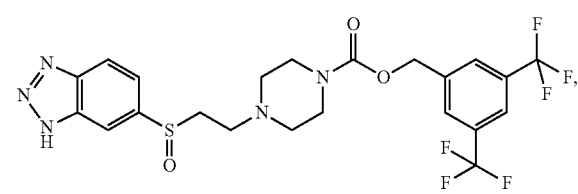

Id

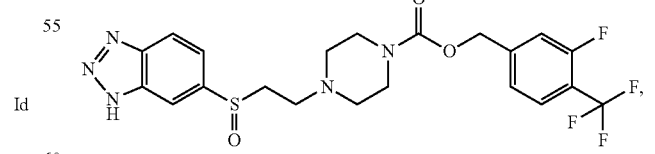

Ik

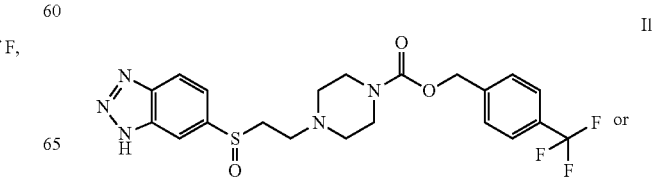

Il or

Im

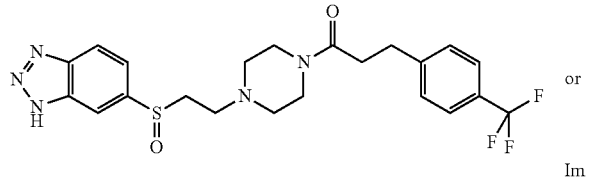

or or a pharmaceutically acceptable salt, enatiomer, tautomer or stereoisomer thereof and (b) an effective amount of a further pharmaceutically active compound.

7. A compound according to claim 1, which is

Ia

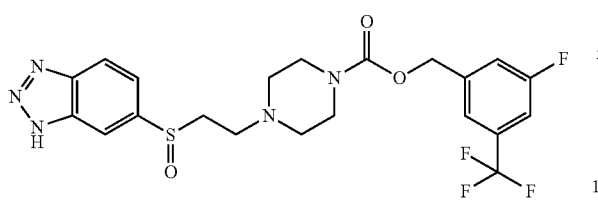

or a pharmaceutically acceptable salt, enatiomer, tautomer or stereoisomer thereof.

8. A compound according to claim 1, which is

Ib

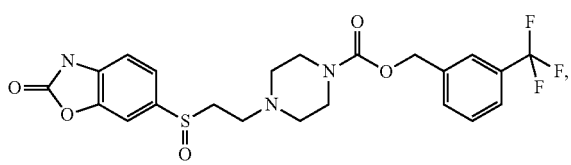

Id

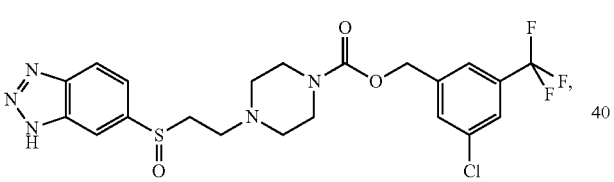

Ij

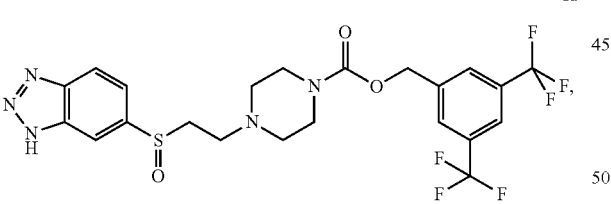

Ik

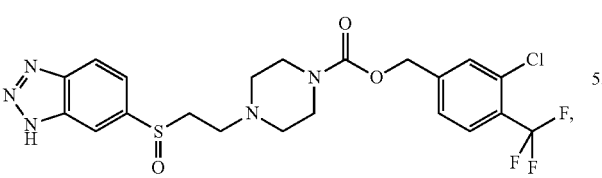

Il

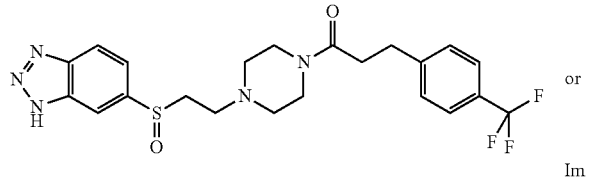

Im

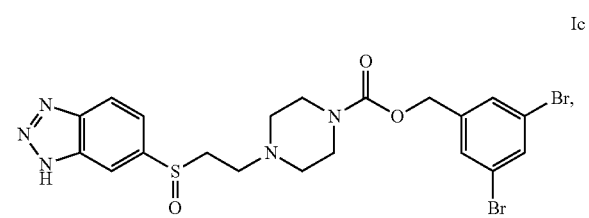

or a pharmaceutically acceptable salt, enatiomer, tautomer or stereoisomer thereof.

9. A compound according to claim 1, which is

Ic

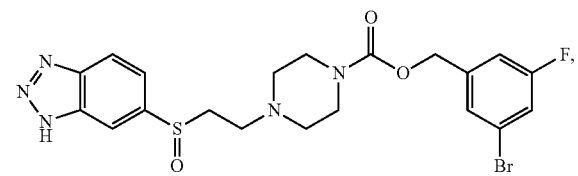

or

Ig

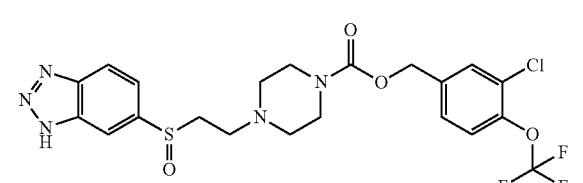

or a pharmaceutically acceptable salt, enatiomer, tautomer or stereoisomer thereof.

10. A compound according to claim 1, which is

If

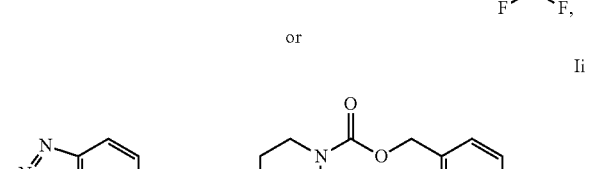

or

Ii

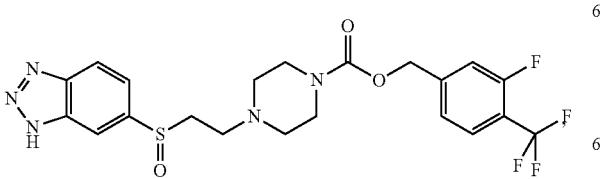

or a pharmaceutically acceptable salt, enatiomer, tautomer or stereoisomer thereof.

11. A compound according to claim 1, which is

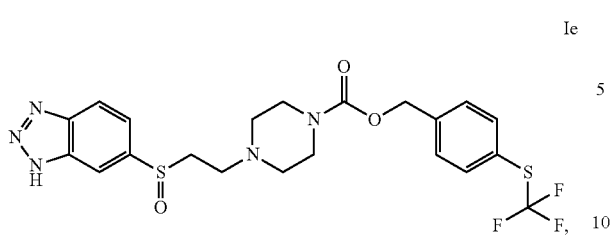

Ie or a pharmaceutically acceptable salt, enatiomer, tautomer or stereoisomer thereof.

12. A compound according to claim 1, which is

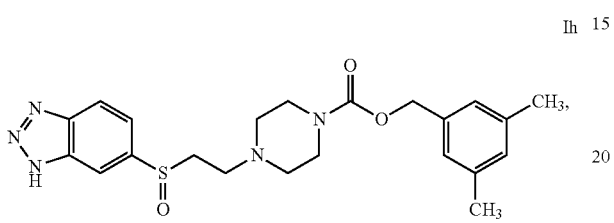

Ih or a pharmaceutically acceptable salt, enatiomer, tautomer or stereoisomer thereof.

13. A method according to claim 3, wherein the disease is ovarian cancer.

14. A method according to claim 3, wherein the disease is hepatoma.

15. A method according to claim 3, wherein the disease is breast cancer.

16. A method according to claim 3, wherein the disease is melanoma.

17. A method according to claim 3, wherein the disease is glioblastoma, lymphoma, leukaemia, colon carcinoma, prostate cancer, renal cell carcinoma, or lung cancer.

18. A method for inhibiting angiogenesis, comprising administering to a subject in need thereof an effective amount of a compound of claim 1.

19. A method for inhibiting autotaxin, comprising bringing together autotaxin with an effective amount of one of the following compounds

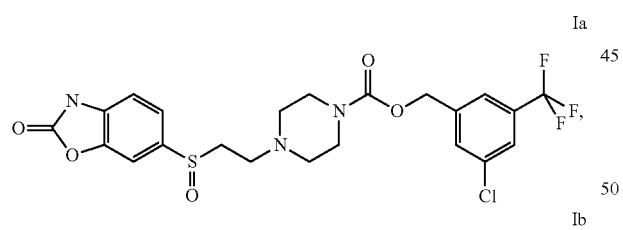

Ia

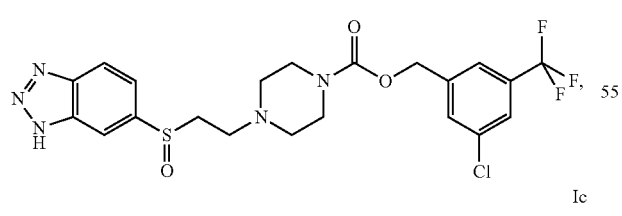

Ib

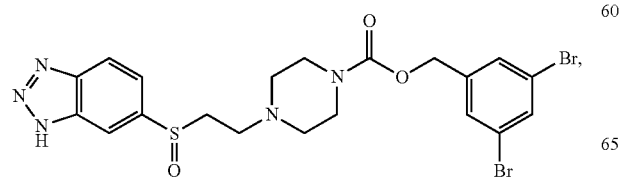

Ic

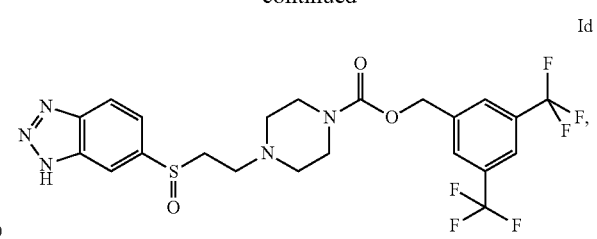

Id

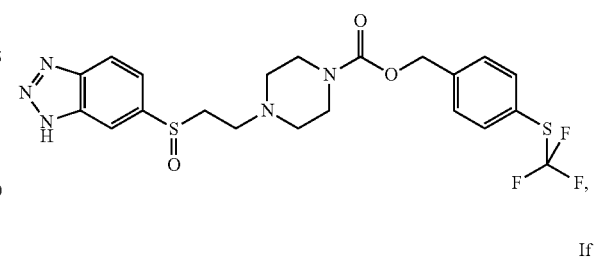

Ie

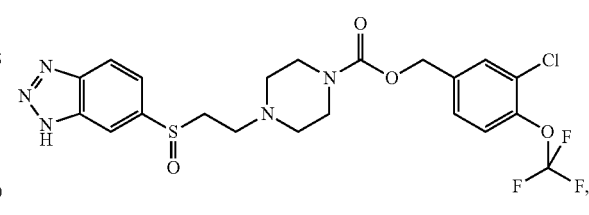

If

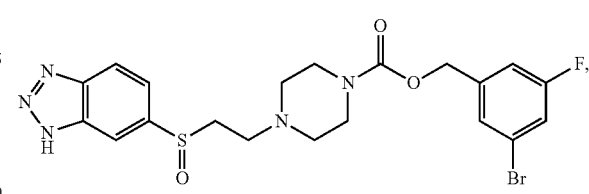

Ig

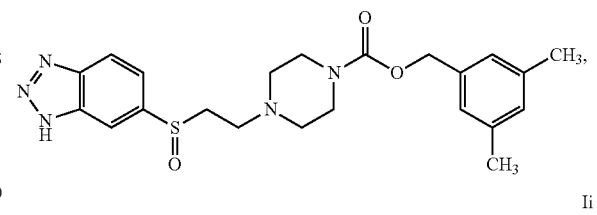

Ih

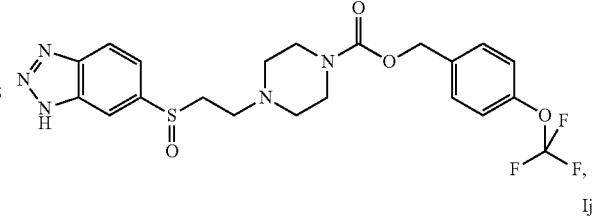

Ii

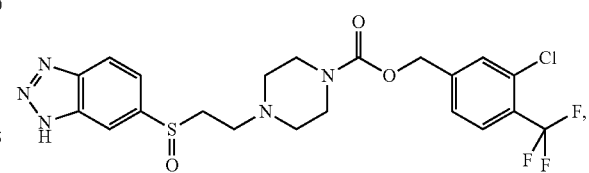

Ij

-continued
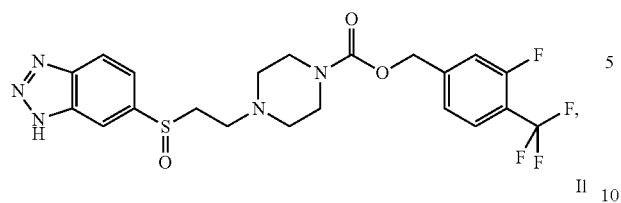
Ik
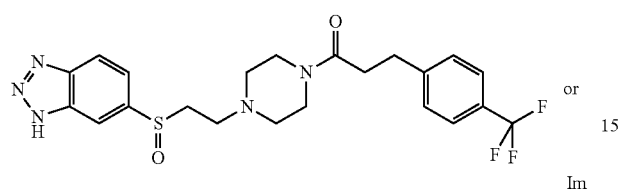
Il
or
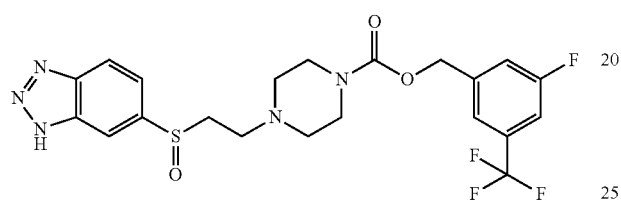
Im
or a pharmaceutically acceptable salt, enatiomer, tautomer or stereoisomer thereof.
20. A method for inhibiting autotaxin according to claim 19, wherein the compound brought together with autotaxin is administered to a subject in need thereof.
* * * * *

UNITED STATES PATENT AND TRADEMARK OFFICE
CERTIFICATE OF CORRECTION

PATENT NO. : 8,552,001 B2  
APPLICATION NO. : 13/501467  
DATED : October 8, 2013  
INVENTOR(S) : Kai Schiemann et al.

Page 1 of 2

It is certified that error appears in the above-identified patent and that said Letters Patent is hereby corrected as shown below:

IN THE CLAIMS:

Column 30, Claim 1, last compound (Compound II) presents as:

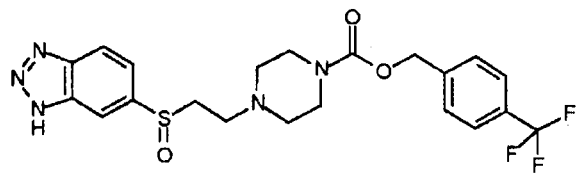

Should present as:

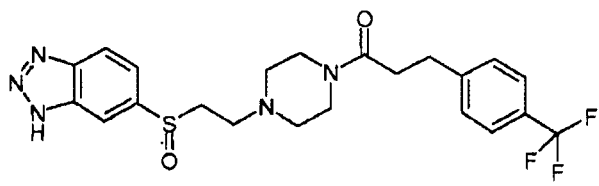

Column 32, Claim 3, second to last compound (Compound II) presents as:

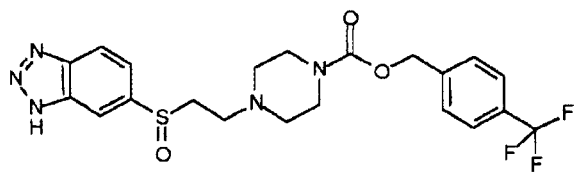

Should present as:

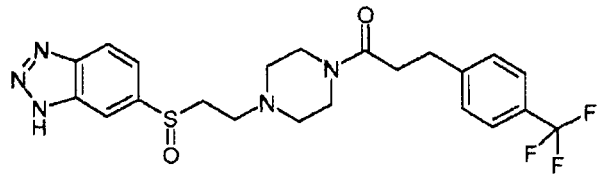

Signed and Sealed this  
Twenty-first Day of October, 2014

Michelle K. Lee  
*Deputy Director of the United States Patent and Trademark Office*

CERTIFICATE OF CORRECTION (continued)
U.S. Pat. No. 8,552,001 B2

IN THE CLAIMS:

Column 34, Claim 6, second to last compound (Compound II) presents as:

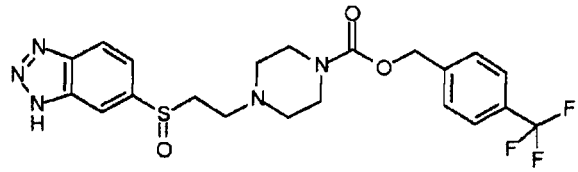

Should present as:

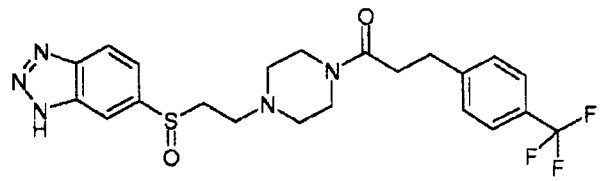

Column 35, Claim 7, Compound Ia presents as:

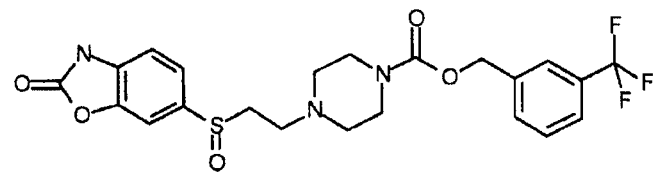

Should present as: